US011151781B2

(12) United States Patent
Mehedy et al.

(10) Patent No.: US 11,151,781 B2
(45) Date of Patent: Oct. 19, 2021

(54) THERAPEUTIC COMB TO CAPTURE IMAGES WITH LIGHT SOURCES

(71) Applicant: INTERNATIONAL BUSINESS MACHINES CORPORATION, Armonk, NY (US)

(72) Inventors: Lenin Mehedy, Doncaster East (AU); Rajib Chakravorty, Epping (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 404 days.

(21) Appl. No.: 16/185,782

(22) Filed: Nov. 9, 2018

(65) Prior Publication Data

US 2020/0151948 A1    May 14, 2020

(51) Int. Cl.
| | | |
|---|---|---|
| G06T 17/00 | (2006.01) | |
| H04N 5/247 | (2006.01) | |
| H04N 5/225 | (2006.01) | |
| A61N 5/06 | (2006.01) | |
| A61B 5/00 | (2006.01) | |
| A61N 5/067 | (2006.01) | |

(52) U.S. Cl.
CPC ............ *G06T 17/00* (2013.01); *A61B 5/0077* (2013.01); *A61B 5/444* (2013.01); *A61B 5/6887* (2013.01); *A61N 5/0616* (2013.01); *H04N 5/2253* (2013.01); *H04N 5/247* (2013.01); *A61N 2005/067* (2013.01); *G06T 2200/08* (2013.01)

(58) Field of Classification Search
CPC ............ A61N 5/0616; A61N 2005/067; A61B 5/6887; A61B 5/444; A61B 5/6814; A61B 5/446
See application file for complete search history.

(56) References Cited

U.S. PATENT DOCUMENTS

| | | | |
|---|---|---|---|
| 7,925,066 B2 | 4/2011 | Ruohonen et al. | |
| 2004/0145656 A1 | 7/2004 | Betra | |
| 2008/0064950 A1 | 3/2008 | Ruohonen et al. | |
| 2015/0164407 A1* | 6/2015 | Hyde .................... | A61B 5/742 |
| | | | 600/301 |

(Continued)

FOREIGN PATENT DOCUMENTS

| | | | |
|---|---|---|---|
| CN | 203563823 U | * | 4/2014 |
| GB | 2120099 B | | 10/1985 |

(Continued)

OTHER PUBLICATIONS

L'Oreal, "Kérastase and Withings Unveil World's First Smart Hairbrush At CES 2017," Research & Innovation, Apr. 2017, 5 pages.

*Primary Examiner* — Serkan Akar
*Assistant Examiner* — Nicholas A Robinson
(74) *Attorney, Agent, or Firm* — Cantor Colburn LLP; Joseph Petrokaitis

(57) ABSTRACT

A technique relates to an imaging apparatus. Extensions are coupled to a support structure, the extensions being spaced a predefined distance from one another, the extensions having a length that protrudes from the support structure. Light sources are coupled to the extensions such that the light sources are positioned to irradiate a scalp. Sensors are coupled to the extensions, the sensors being positioned at an angle to capture images of the scalp having been irradiated by the light sources.

17 Claims, 8 Drawing Sheets

(56) References Cited

U.S. PATENT DOCUMENTS

2016/0106999 A1\* 4/2016 Michaels .............. A61M 37/00
604/20

FOREIGN PATENT DOCUMENTS

| | | |
|---|---|---|
| GB | 2204231 B | 11/1990 |
| KR | 1362357 B1 \* | 10/2012 |
| KR | 101351056 B1 | 1/2014 |
| KR | 20150059953 A | 6/2015 |
| KR | 101536700 B1 | 7/2015 |
| KR | 20170088174 A | 8/2017 |

\* cited by examiner

THERAPEUTIC COMB TO CAPTURE IMAGES WITH LIGHT SOURCES

BACKGROUND

The present invention generally relates to methods and devices for images, and more specifically, to a scanner to capture images and three dimensional (3D) model generation.

In humans, the scalp is the anatomical area bordered by the face at the front and by the neck at the sides and back. The scalp is the skin on the head from which head hair grows. There can be various types of scalp diseases or issues that can occur on a person's head. In order to evaluate the topology of a person's scalp, visualization of the person's scalp has to be obtained, which allows diagnosis of the potential scalp disease or issue.

SUMMARY

Embodiments of the invention are directed to a method of forming an imaging apparatus. A non-limiting example of the method includes providing extensions coupled to a support structure, the extensions being spaced a predefined distance from one another, the extensions having a length that protrudes from the support structure. The method includes coupling light sources to the extensions such that the light sources are positioned to irradiate a scalp and coupling sensors to the extensions, the sensors being positioned at an angle to capture images of the scalp having been irradiated by the light sources.

Embodiments of the invention are directed to an imaging apparatus. A non-limiting example of the apparatus includes extensions coupled to a support structure, the extensions being spaced a predefined distance from one another, the extensions having a length that protrudes from the support structure. The apparatus includes light sources coupled to the extensions such that the light sources are positioned to irradiate a scalp and sensors coupled to the extensions, the sensors being positioned at an angle to capture images of the scalp having been irradiated by the light sources.

Embodiments of the invention are directed to a method of operating an imaging apparatus. A non-limiting example of the method includes receiving, by the comb apparatus, location reference signals. The method includes capturing, by sensors of the comb apparatus, images of a scalp at different locations on the scalp, the different locations being determined based on the location reference signals, the images being captured under illumination from light sources of the comb apparatus. Also, the method includes providing a model of the scalp according to the images captured at the different locations on the scalp.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the embodiments of the invention, the various elements illustrated in the figures are provided with two or three digit reference numbers. With minor exceptions, the leftmost digit(s) of each reference number correspond to the figure in which its element is first illustrated.

DETAILED DESCRIPTION

Turning now to an overview of technologies that are more specifically relevant to aspects of the invention, scalp images are difficult to capture because of long hair. It is also not feasible to shave hair each time a scalp image is needed. Scalp images (i.e., of the skin) always have the impurity of hair being on the area of interest (e.g. mole). This adds additional complexity to analyzing the image using machine learning algorithms (which can use, e.g., training data, learning algorithms, classifiers, etc.) because the underlying skin area might not be clearly visible.

Embodiments of the present invention provide a method and device as a scalp scanner equipped with sensors, light emitting diodes (LEDs) (light sources that can emit different types of light on demand, such as red, green, blue (RGB), infrared, etc.), and cameras embedded on a comb, such that the comb can take images of the skin on the scalp from different angles and with different light configurations for diagnosis and 3D model generation. In order to make location estimations, reference signal transmitters can be placed at predetermined locations. The reference signal transmitters can be embedded in wearable structures such as earrings or a necklace.

Figure 1:
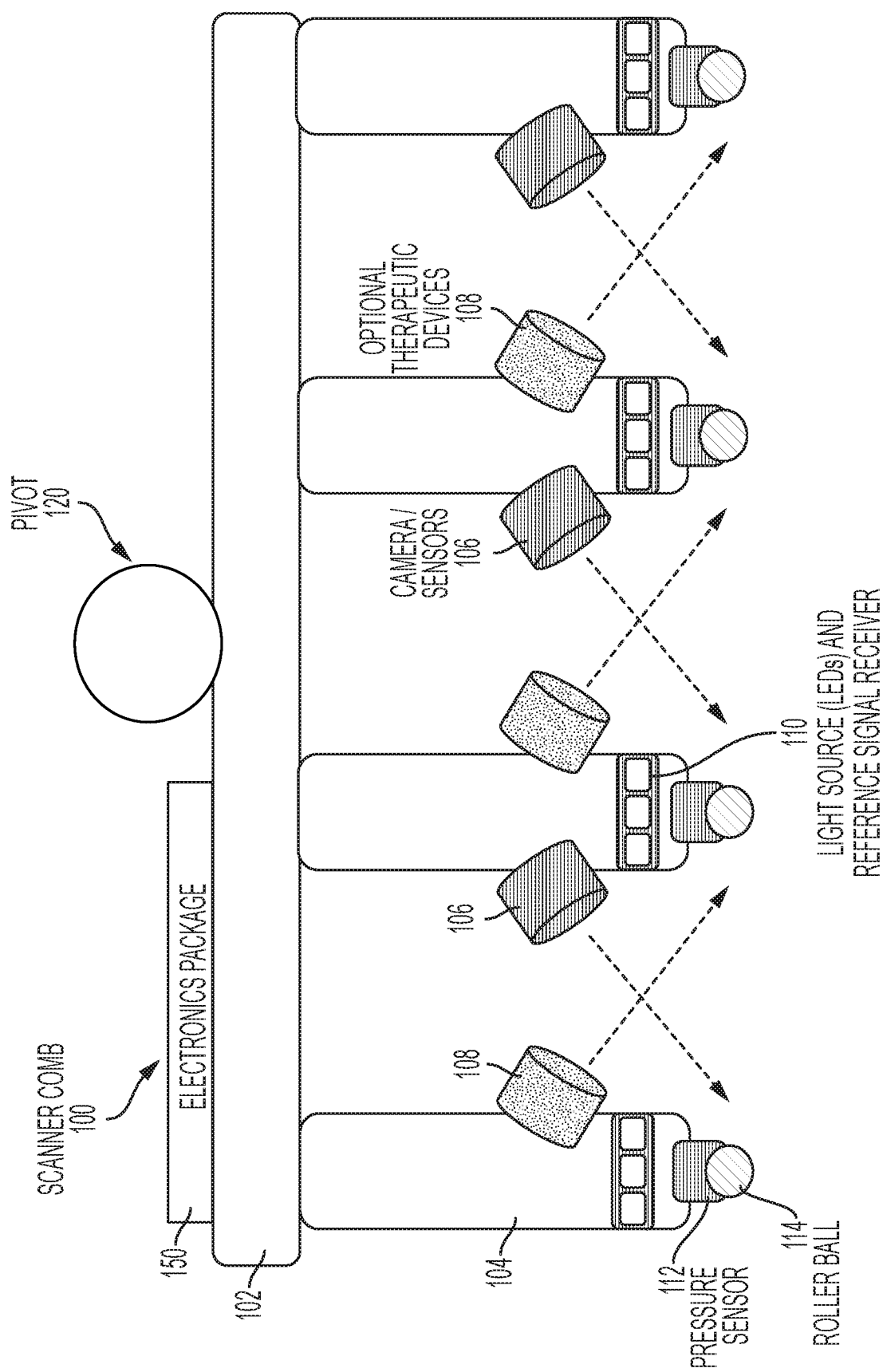
FIG. 1 depicts a side view of an imaging device according to embodiments of the invention.
Figure 6:
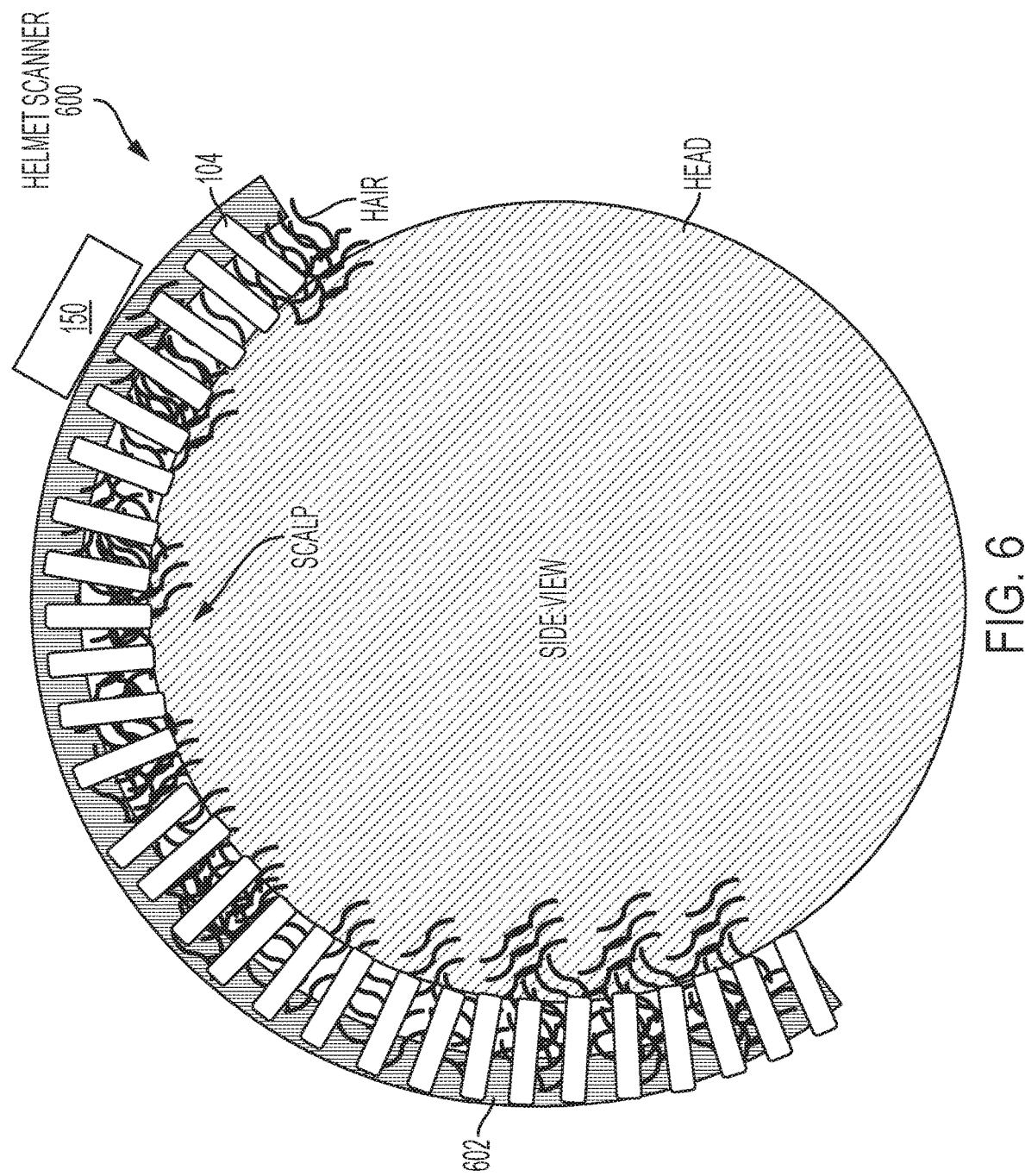
FIG. 6 depicts a side view of a helmet scanner which integrates elements of the comb imaging device according to embodiments of the invention.

Turning now to a more detailed description of aspects of the present invention, FIG. 1 depicts a side view of an imaging device 100 according to embodiments of the invention. The imaging device 100 can be a scanner comb, scanner brush, and/or scalp scanner according to embodiments of invention. The imaging device 100 includes a support structure 102 having extensions 104. The discussion of imaging device 100 applies by analogy to support structure 602 also having extensions 104 in the head scanner helmet 600 as depicted in FIG. 6.

The support structure 102 is a base structure from which the extensions 104 extend. The extensions 104 can be teeth, tips, prongs, etc., which are spaced a predefined distance apart and are configured to separate hair on a person's head. The predefined distance of the spacing between extensions 104 can range from 1 mm to 20 mm, which can depend on the availability of miniature cameras and other parts at the time of manufacturing. The support structure 102 and extensions 104 can be made of any suitable material. In some implementations, the material can be the same for the support structure 102 and extensions 104, and in some implementations, the material can be different for the support structure 102 and extensions 104. Example materials can include plastic, wood, ceramics, glass, metals, metalloids, composite materials, etc., and/or combinations of the materials. The support structure 102 and extensions 104 can be formed from a mold, for example, by using injection molding. There can be various ways to attach extensions 104 to the support structure 102. For example, the extensions 104 can be screwed in and/or inserted into predefined holes in the support structure 102. Adhesives can be used to attach the extensions 104 to the support structure 102. The can be one or more slots in the support structure 102 formed to laterally receive a plate that holds the extensions 104.

Each of the extensions 104 can include individual cameras/sensors 106, individual light sources 110, individual pressure sensors 112, individual roller balls 114, and (optionally) individual therapeutic devices 108. The comb tips/extensions 104 of the comb imaging device 100 has pressure sensors 112 and roller balls 114 for comfort to the user. Readings from the pressure sensor 112 can be used to model the terrain of the scalp and stored in memory 720 depicted in FIG. 7. For subsequent passes of the scalp with the pressure sensors 112, the readings from the pressure sensors 112 can be utilized to measure the outward growth of a mole on the scalp if we have previous readings of the same scalp for comparison. A pivot 120 can be attached to the comb imaging device 100, and the pivot can be used for attaching to another structure.

The cameras/sensors 106 are configured to individually capture images of the scalp as the extensions 104 comb through and/or separate the hair. Particularly, the extensions 104 have multiple cameras 106 placed at angles to take pictures of a spot from different directions. For example, images of the same spot on the scalp are taken by the multiple cameras 106 as the user combs through her/his hair. Although one camera 106 is illustrated on each extension 104 in the side view in FIG. 1, it should be appreciated that another camera 106 can be located on the back side of the extension 104. Examples of the cameras/sensors 106 can include charge coupled devices (CCD), active pixel sensors (APS) including CMOS sensors, photodiodes, etc. Other types of imaging devices can also be utilized.

The comb tips/extensions 104 each can include a light source 110 as noted above, and the light sources 110 can be light emitting diodes (LEDs) (including red, blue green (RGB)), infrared, ultraviolet (UV), and/or other types of light sources such that the cameras/sensors 106 can capture images with different types of light which can improve visualization and/or identification of skin issues/diseases (i.e., problems) on the scalp. The light sources 110 and cameras/sensors 106 can be in pairs, such as a light source 110 is positioned/angled to illuminate the same spot on the scalp for which a corresponding camera/sensor 106 is positioned/angled to capture an image of. In some cases, the extensions 104 can be removable such that they can be replaced when any part on the extension is malfunctioning. For example, each extension 104 can be replaced when any one or more of its the cameras/sensors 106, therapeutic devices 108, light sources 110, pressure sensors 112, roller balls 114 is inoperable.

Figure 7:
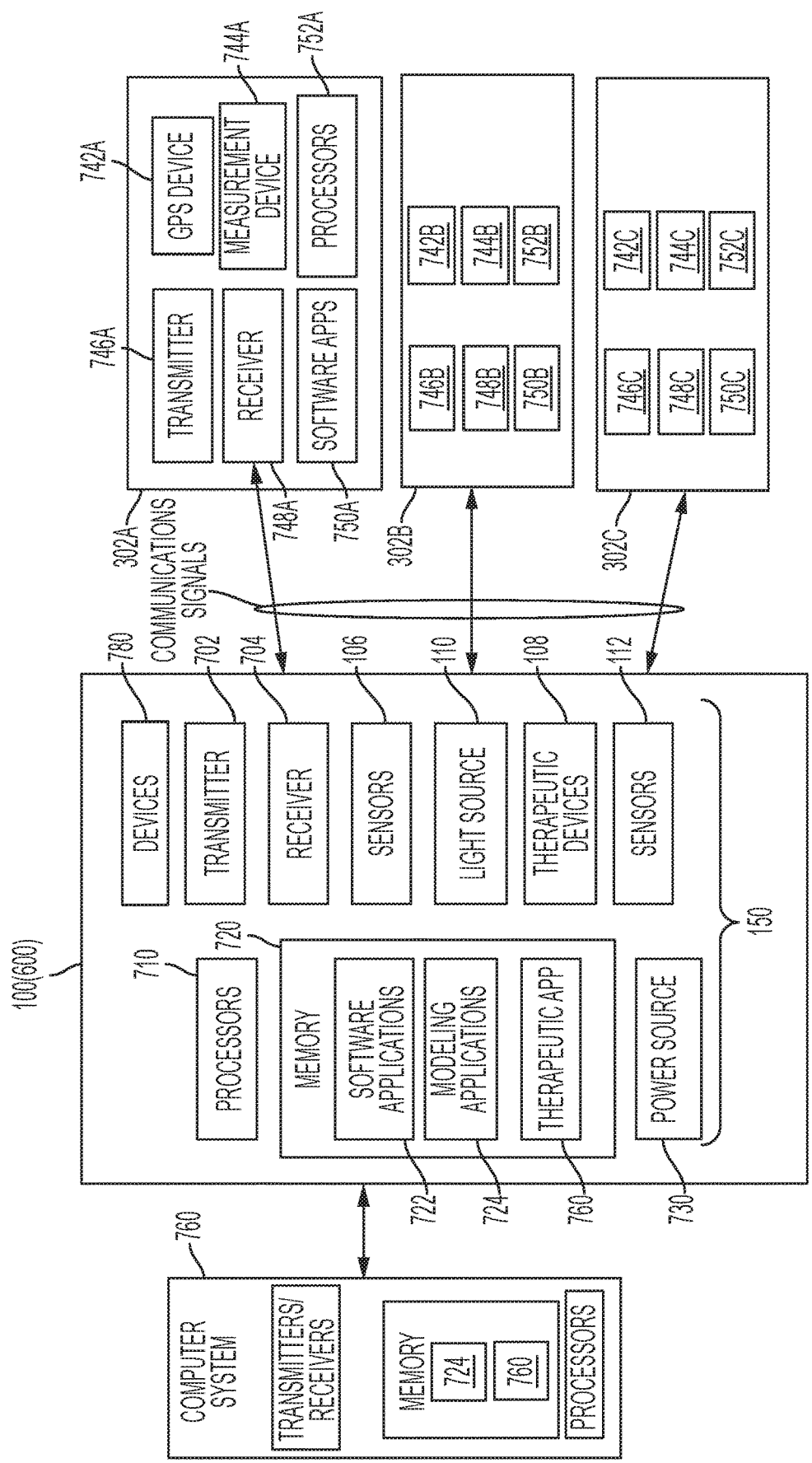
FIG. 7 depicts a block diagram of a system according to embodiments of the invention.

Additionally, the imaging device 100 can include an electronics package 150. The electronics package 150 can include transmitters 702, receivers 704, processors 710, memory 720, software applications 722, (optionally) 3D modeling applications 724, power sources 730, and input/output devices 780 (display screen (e.g., touch screen), speakers, joystick, keys, etc.) as depicted in FIG. 7. The power source 730 provides power to the imaging device 100 (as well as the helmet scanner 602 depicted in FIG. 6). The power source 730 can be a portable battery, a plug to a wall outlet, etc. The software application 722 communicates with and can run a diagnostics on the cameras/sensors 106, therapeutic devices 108, light sources 110, and pressure sensors 112. As such, the software application 722 is configured to alert the user when any part is inoperable, for example, via a beep sound, a display screen, etc., such that the corresponding extension 104 can be replaced.

Figure 2A:
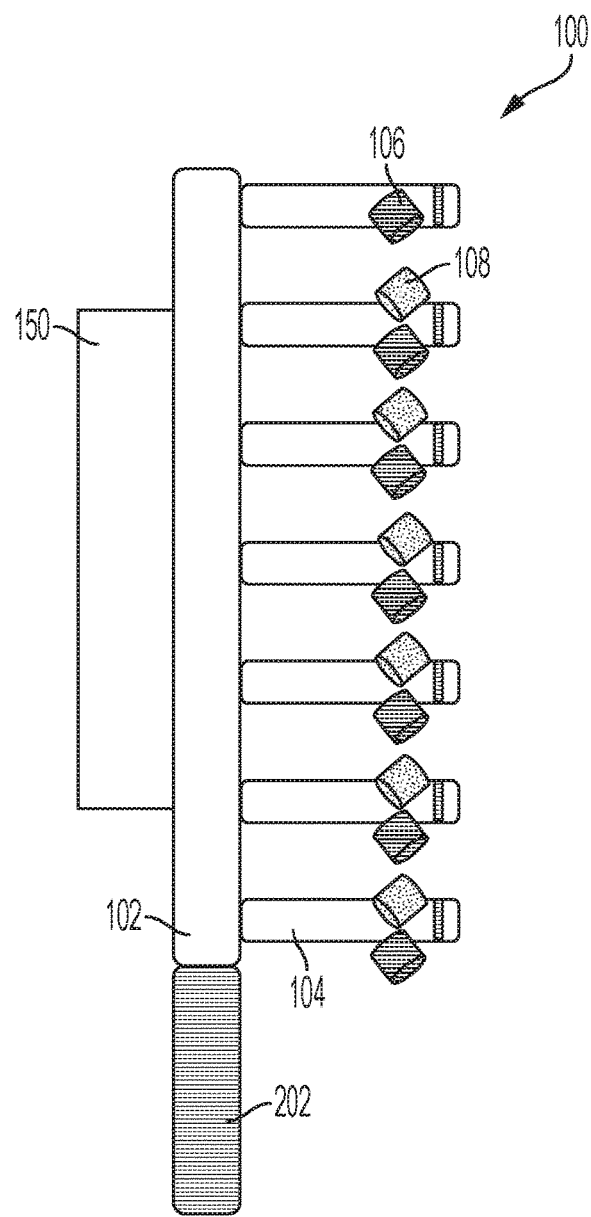
FIG. 2A depicts the imaging device with a handle according to embodiments of the invention.
Figure 2B:
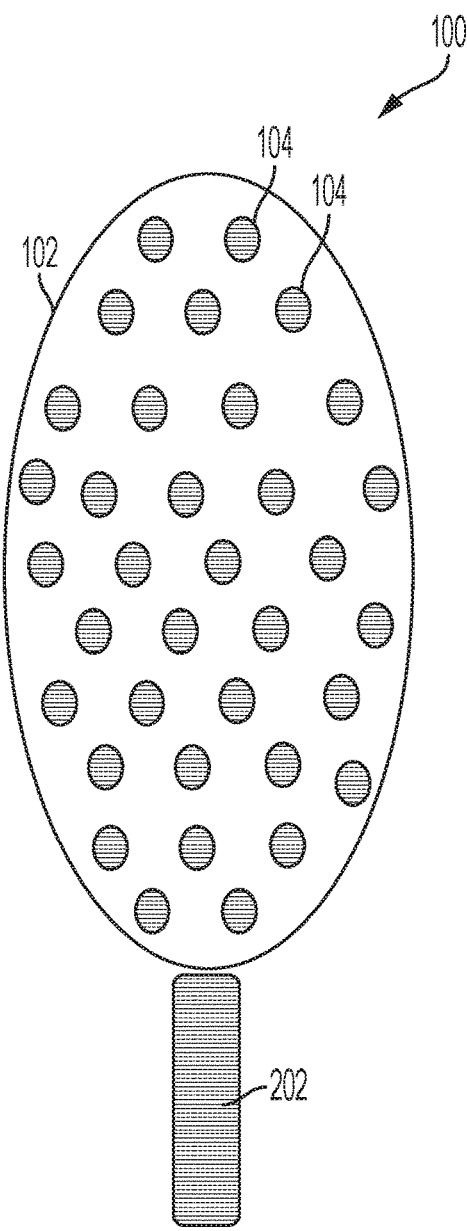
FIG. 2B depicts the imaging device with a wide support structure according to embodiments.

FIG. 2A depicts the imaging device 100 with a handle 202 according to embodiments of the invention. FIG. 2B depicts the imaging device 100 as a brush in which the support structure 102 is wide surface capable of accommodating various arrangements of extensions 104 according to embodiments. The details of the extensions 104 are not illustrated in FIGS. 2A and 2B so as not to obscure the figures.

Figure 3:
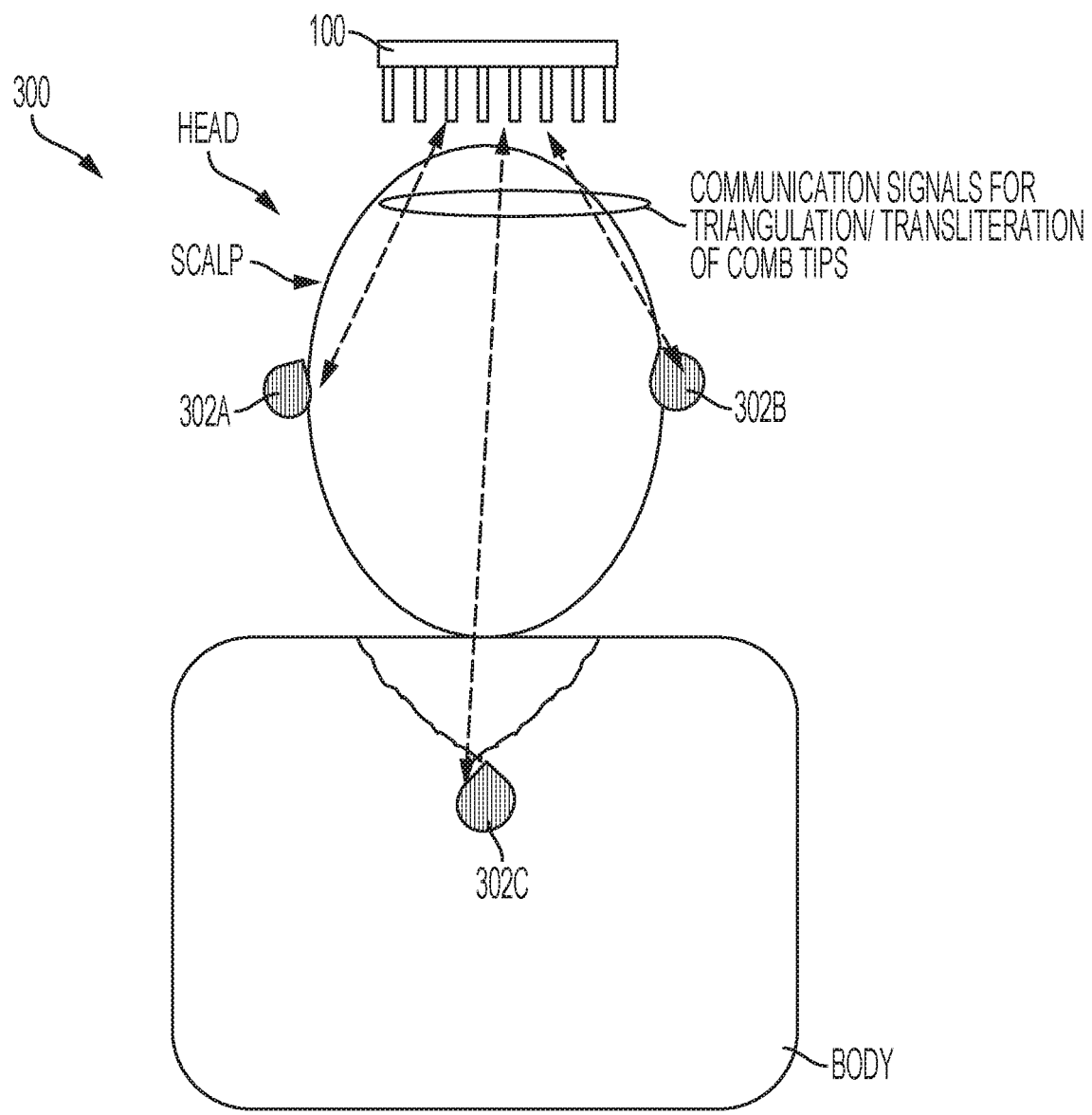
FIG. 3 depicts a system according to embodiments of the invention.

FIG. 3 depicts a system 300 according to embodiments of the invention. The system 300 includes the comb/brush imaging device 100 and at least three reference signal transmitters 302A, 302B, and 302C. For explanation purposes, FIG. 3 shows reference signal transmitters 302A and 302B as earrings and reference signal transmitter 302C as a necklace. Each of the reference signal transmitters 302A, 302B, and 302C is configured to know its present location, and each reference signal transmitter 302A, 302B, and 302C can transmit its respective location to the receiver 704 of the imaging device 100. In some implementations, the software application 722 executed by processors 710 is configured to know in advance the predefined location of each one of the extensions 104 and the respective spacing between the extensions 104. The software application 722 is configured to receive the three locations of the reference signal transmitters 302A, 302B, and 302C. The software application 722 determines the location of the imaging device 100 using the three known locations of the reference signal transmitters 302A, 302B, and 302C, for example, using triangulation, trilateration, and/or any method known to one skilled in the art. Once the imaging device 100 determines its position/location, the software application 722 of imaging device 100 uses this position/location to identify each individual location of the cameras/sensors 106 on extensions 104 because the spacing and location of each extension 104 is known in advance. Alternatively and/or additionally, in some implementations, each comb tip/extension 104 (having its own transmitter 702/receiver 704) can (also) capture the reference signal and each comb tip/extension 104 calculates (via software application 722) its location using triangulation. As such, each extension 104 has its own receiver to receive the reference location signals from the reference signal transmitters 302A, 302B, and 302C.

Accordingly, the location and spot on the scalp at which each image/picture is captured by each of the cameras/sensors 106 on the respective extensions 104 is determined and known by the software application 722. The software application 722 is configured to store each of the captured images and their respective locations when captured on the scalp (e.g., like a grid) in memory 720. As such, the software application 722 is configured to reconstruct a grid of the scalp using the multiple images captured by the cameras/sensors 106 along with their respective locations when captured on the scalp.

The software application 722 can be integrated with, communicate with, and/or include the 3D modeling software application 724. The software application 722 can send the images (which include multiple images of the same spot on the scalp taken from different directions) to the 3D modeling software application 724. The 3D modeling software application 724 is configured to create a 3D model of the scalp of the person. In some implementations, the software application 722 can send the images to a remote computer system 760, and the computer system 760 can include the 3D modeling software application 724. The 3D modeling software application 724 on computer system 760 can create the 3D image of the scalp using the captured images (and their respective locations when captured on the scalp) sent from software application 722. The computer system 760 can send the 3D image back to the comb imaging device 100 for further use.

Figure 4:
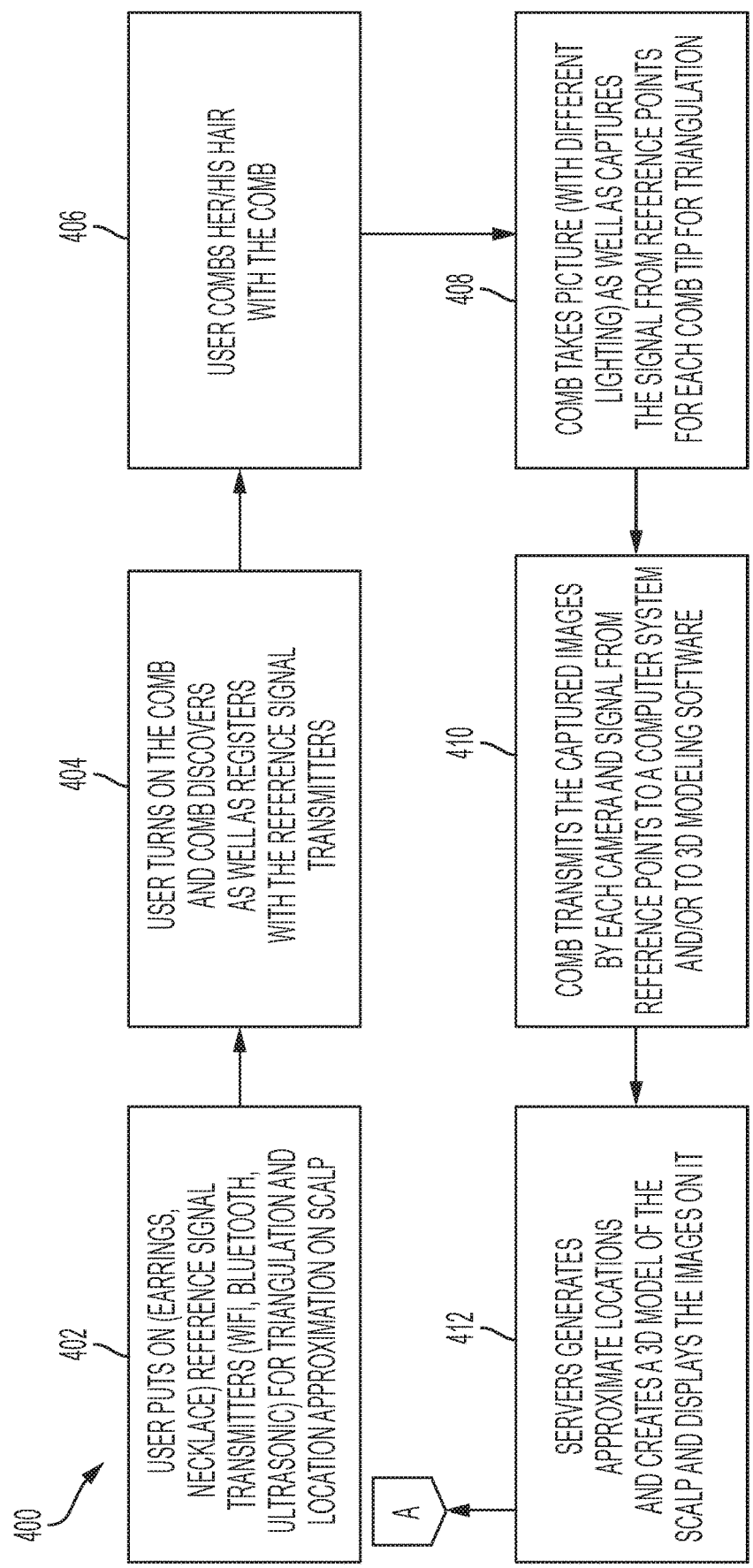
FIG. 4 depicts a flow chart of a method of image capture and 3D model generation for the scalp according to embodiments of the invention.

FIG. 4 depicts a flow chart 400 of a method of image capture and 3D model generation for the scalp using the imaging device 100 and/or helmet scanner 600 according to embodiments of the invention. At block 402, the user can put on the reference signal transmitters 302A, 302B, 302C and activate the reference signal transmitters 302A, 302B, 302C for reference signal transmission to the comb imaging device 100. As an example, the user can put on or attach earrings and a necklace as the reference signal transmitters 302A, 302B, 302C illustrated in FIG. 3, the reference signals can be transmitted wirelessly over Wi-Fi®, Bluetooth®, etc., and/or can be ultrasonic signals for triangulation and location approximation on scalp. Also, the reference signals from reference signal transmitters 302A, 302B, 302C can be transmitted over a wired connection, such as USB cables, etc. In some cases, two reference signal transmitters 302A and 302B can be attached, clamped, and/or clipped on the shoulders of clothing while reference signal transmitter 302C is attached, clamped, and/or clipped on the collar or neck of clothing.

At block 404, the comb imaging device 100 is activated, and the software application 722 discovers and registers (via transmitter 702 and receiver 704) with the reference signal transmitters 302A, 302B, 302C. The software application 722 (continuously) receives three reference signals from reference signal transmitters 302A, 302B, 302C and processes the reference signals to determine the location of the comb imaging device 100 as the user combs her/his hair with the comb imaging device 100, at block 406.

At block 408, the cameras/sensors 106 take pictures (with different lighting emitted by the light sources 110) of the scalp while the software application 722 (continuously) captures the reference signals from reference points (i.e., reference signal transmitters 302A, 302B, 302C) for each comb tip/extension 104 for triangulation. The images are captured all while the user combs her/his hair. In some implementations, the software application 722 is configured to cause the cameras/sensors 106 to continuously captures images as along as least one of the pressure sensors 112 sends a pressure sensor signal to the software application 722, which is indicative of at least one pressure sensor 112 contacting hair and/or the scalp.

At block 410, the software application 722 of comb imaging device 100 transmits the captured images having been captured by each camera 106 and reference signal (including location at which each image was captured) to a computer system 760 and/or to 3D modeling software 724 (which can be in memory 720 of the imaging device 100 itself). The location at which the captured image was taken can be X and Y coordinates relative to X and Y coordinates of other captured images.

At block 412, the 3D modeling software 724 which can be in the computer system 760 and/or in the comb imaging device 100 generates approximate locations (e.g., and X and Y grid) and creates a 3D model of the scalp, and the 3D modeling software 724 is configured to display the captured images on/in the 3D model of the scalp.

Creating a 3D model from images of the same area captured from different angles is understood by one skilled in the art. As one example, point cloud technology can be used, where a point cloud is a set of data points in space. Point clouds are generally produced by scanners, which measure a large number of points on the external surfaces of objects around them. For example, a series of photos or images of an area on the scalp is captured, and the 3D modeling software 724 automatically matches the images and then calculates positions in space from which each image has been taken along with a 3D point cloud of the scene. While point clouds can be directly rendered and inspected, point clouds are often converted to polygon mesh or triangle mesh models, NURBS surface models, or CAD models through a process commonly referred to as surface reconstruction, via the 3D modeling software 724.

Figure 5:
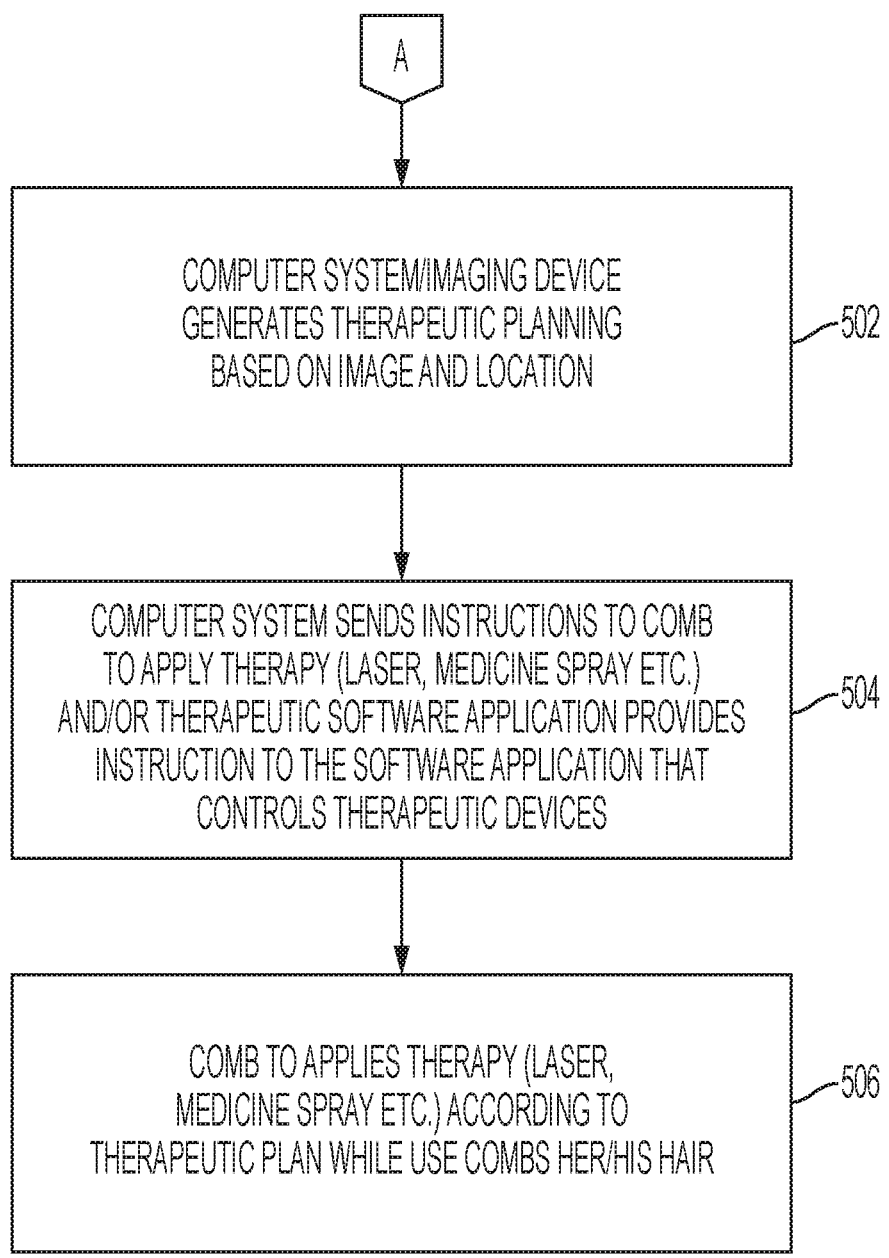
FIG. 5 depicts a flow chart of therapeutic treatment for the imaging device according to embodiments of the invention.

FIG. 5 depicts a flow chart 500 of a therapeutic administration or treatment for use by the imaging device 100 (and/or helmet scanner 600) according to embodiments of the invention. The flow from FIG. 4 can continue to FIG. 5. Given the grid and/or 3D model of the scalp, a therapeutic software application 760 (which can be executed on the computer system 760, imaging device 100, and/or helmet scanner) is configured to generate therapeutic planning based on the capture images and their respective locations on the scalp and determine treatment instructions for the skin issue/disease, at block 502.

At block 504, computer system 760 sends treatment instructions to comb imaging device 100 to apply therapy (laser, medicine spray, etc.) to the skin issue/disease and/or therapeutic software application 760 provides treatment instructions to the software application 722 that controls therapeutic devices 108.

At block 506, the software application 722 is configured to apply/execute the treatment instructions (laser, medicine spray, etc., via the therapeutic devices 108) to the scalp according to the therapeutic plan while the user combs her/his hair with the comb imaging device 100. The treatment instructions are configured apply the treatment to the particular location of the scalp issue/disease as determined therapeutic planning. For example, the therapeutic devices 108 can contain medicine and nozzles to automatically spray the medicine when the user moves the comb/imaging device 100 to the particular location(s) on the scalp, because the software application 722 has a grid and/or 3D model of the scalp in order to apply the treatment at the proper locations on the scalp. As noted above, the treatment can be laser treatment applied to irradiate the scalp at a predefined wavelength.

There are various methods of how the therapeutic software application 760 diagnoses the skin and determines the treatment instructions. The process of the therapeutic software application 760 (in conjunction with the software application 722 and/or modeling applications 724 and/or in conjunction with the output from the software application 722 and/or modeling applications 724) can include the following operations.

1. Given the 3D model of the scalp, the software applications 760 (and/or software applications 722, 724) measures various parameters of the disease area such as shape changes, color changes, and/or growth of the area compared to previous scans of the patient, and/or a database of patients. The database can be in memory 720 and/or memory of the computer system 760.

2. Depending on the measurements in operation 1, the software applications 760 (and/or software applications 722, 724) selects a pre-defined treatment plan and/or requests a clinician to input a treatment plan into the database by filling up a form and/or selecting a predefined plan for access by software application 760 (and/or software applications 722, 724).

3. The treatment plan is then converted into machine readable format (if new) as JSON, XML, etc., which can be sent over to the device 100, 600 through a communication channel if the device 100, 600 does not develop the treatment plan itself. An example JSON could be the following.

```
{
    "location": {
        "x": 24,
        "y": 56,
        "z": 5,
    },
    "therapy:"
        "laser54":{
            "action":"blink",
            "time": 2ms
        },
        "spray55":{
            "action":"on",
            "time": 3ms
        }
    }
}
```

4. Upon receiving the instruction as JSON as above, the device 100, 600 detects the location and turns on the therapeutic instruments based on the instructions.

FIG. 6 depicts a side view of a helmet scanner 600 which integrates elements of the comb imaging device 100 according to embodiments of the invention. The details of cameras/sensors 106, therapeutic devices 108, and light sources 110 are present but not illustrated in FIG. 6 so as not to obscure the figure. Just as discussed for the comb imaging device 100, the cameras/sensors 106 on the helmet scanner 600 are configured to capture the images of the scalp and store the images in the memory 720. Also, the helmet scanner 600 can send the images to the computer system 760 as discussed herein for the comb imaging device 100.

FIG. 7 depicts a block diagram of a system according to embodiments of the invention. To implement embodiments of the invention discussed herein, the computer system 760 (which can be a remote server, a mobile device such as cellphone, a laptop, etc.), the imaging device 100, the helmet scanner 600, and the reference transmitters 302A, 302B, 302C can include any of the elements/functions discussed in a computer system 812 depicted in FIG. 8.

In some implementations, the imaging device 100 and/or helmet scanner 600 can perform the 3D modeling (via 3D modeling software application 724) to create a 3D model of the scalp including the skin disease/issue, perform the therapeutic planning (via therapeutic software application 760) to resolve or address the skin disease/issue, and provide the treatment instructions to the software application 722 to perform the treatment instructions via therapeutic devices 108.

In some implementations, the imaging device 100 and/or helmet scanner 600 can communicate with the computer system 760 over a network. To offload some of the processing to the computer system 760, the computer system 760 can perform the 3D modeling (via its 3D modeling software application 724) to create a 3D model of the scalp including the skin disease/issue, perform the therapeutic planning (via its therapeutic software application 760) to resolve or address the skin disease/issue, and provide the treatment instructions to the software application 722 (of the imaging device 100 and/or helmet scanner 600) to perform the treatment instructions via therapeutic devices 108.

Also, FIG. 7 illustrates the imaging device 100 communicating with the reference transmitters 302A, 302B, 302C, generally referred to as reference transmitters 302. Each of the reference transmitters 302 can have its own GPS device 742A, 742B, 742C which determine location, measurement device 744A, 744B, 744C which can measure distance (e.g., in X, Y, Z coordinates using lasers) to more precisely determine its exact location within a room, transmitter 746A, 746B, 746C, receiver 748A, 748B, 748C, and processors 752A, 752B, 752C to execute software applications 750A, 750B, 750C containing instructions to perform as discussed herein. The reference signal transmitters 302A, 302B, 302C can each include a power source (not shown), such as a portable battery, plug to a wall outlet, etc.

According to embodiments of the invention, a method of forming an apparatus 100, 600 for a scalp of the head is provided. The method includes providing extensions 104 coupled to a support structure 102, 602, the extensions 104 being spaced a predefined distance from one another, the extensions 104 having a length that protrudes away from the support structure 102, 602. The method include coupling light sources 108 to (each of) the extensions such that the light sources 110 are positioned to irradiate (individual spots on) the scalp. The method includes coupling sensors 106 to the (each of the) extensions 104, the sensors 106 being positioned at an angle to capture images of the scalp (at the individual spots) having been irradiated by the light sources 110.

The extensions 104 are spaced the predefined distance from one another so as to accommodate combing through hair on the scalp. The light sources 110 are coupled to a distal end of the extensions 104. The light sources 110 are positioned at a distance greater than half the length away from the support structure. Being closer to the scalp than the support structure 102, 602 helps to illuminate the skin on the scalp without the light be obscured by hair. Accordingly, having light sources 110 positioned on distal end of the extensions 104 and/or at a distance greater than half the length away from the support structure 102, 602 is an improvement over having a light source positioned (directly) on the support structure.

The cameras/sensors 106 are coupled to a distal end of the extensions 104. The cameras/sensors 106 are positioned at a distance greater than half the length away from the support structure. Similarly, being closer to the scalp than the support structure 102, 602 helps to capture images of the scalp (i.e., the skin on the scalp) without the images be obscured by hair. Accordingly, having cameras/sensors 106 positioned on distal end of the extensions 104 and/or at a distance greater than half the length away from the support structure 102, 602 is an improvement over having a camera positioned (directly) on the support structure.

Therapeutic devices 108 are coupled to the extensions 104. Therapeutic devices 108 are positioned at a distance greater than half the length away from the support structure 102, 602. Therapeutic devices 108 are positioned at an angle on the extensions 104 to medically treat areas (at the individual spots) of the scalp. Similarly, being closer to the scalp than the support structure 102, 602 ensures that the medical treatment administered by therapeutic devices 108 is (directly) on the scalp (i.e., skin on the scalp) without the being blocked/obscured by hair. Accordingly, having therapeutic devices 108 positioned on distal end of the extensions 104 and/or at a distance greater than half the length away from the support structure 102, 602 is an improvement. Roller balls 114 are coupled to ends of the extensions 104.

According to embodiments of the invention, a method of operating a comb apparatus 100, 600 for a scalp of the head according to embodiments of the invention. The method includes receiving, by the comb apparatus 100, 600, location reference signals (from reference transmitters 302A, 302B, 302C). The method includes capturing, by sensors 106 of the comb apparatus 100, 600, images of the scalp at different locations on the scalp, the different locations being determined based on the location reference signals, the images being captured under illumination from light sources 110 of the comb apparatus 100, 600. The method includes providing a model (via modeling software application 724) of the scalp according to the images captured at the different locations on the scalp.

The method includes receiving a treatment plan (by the therapeutic software application 760) for the scalp according the model, and causing therapeutic devices 760 of the comb apparatus 100, 600 to apply medical treatment to the scalp according to instructions of the treatment plan.

Figure 8:
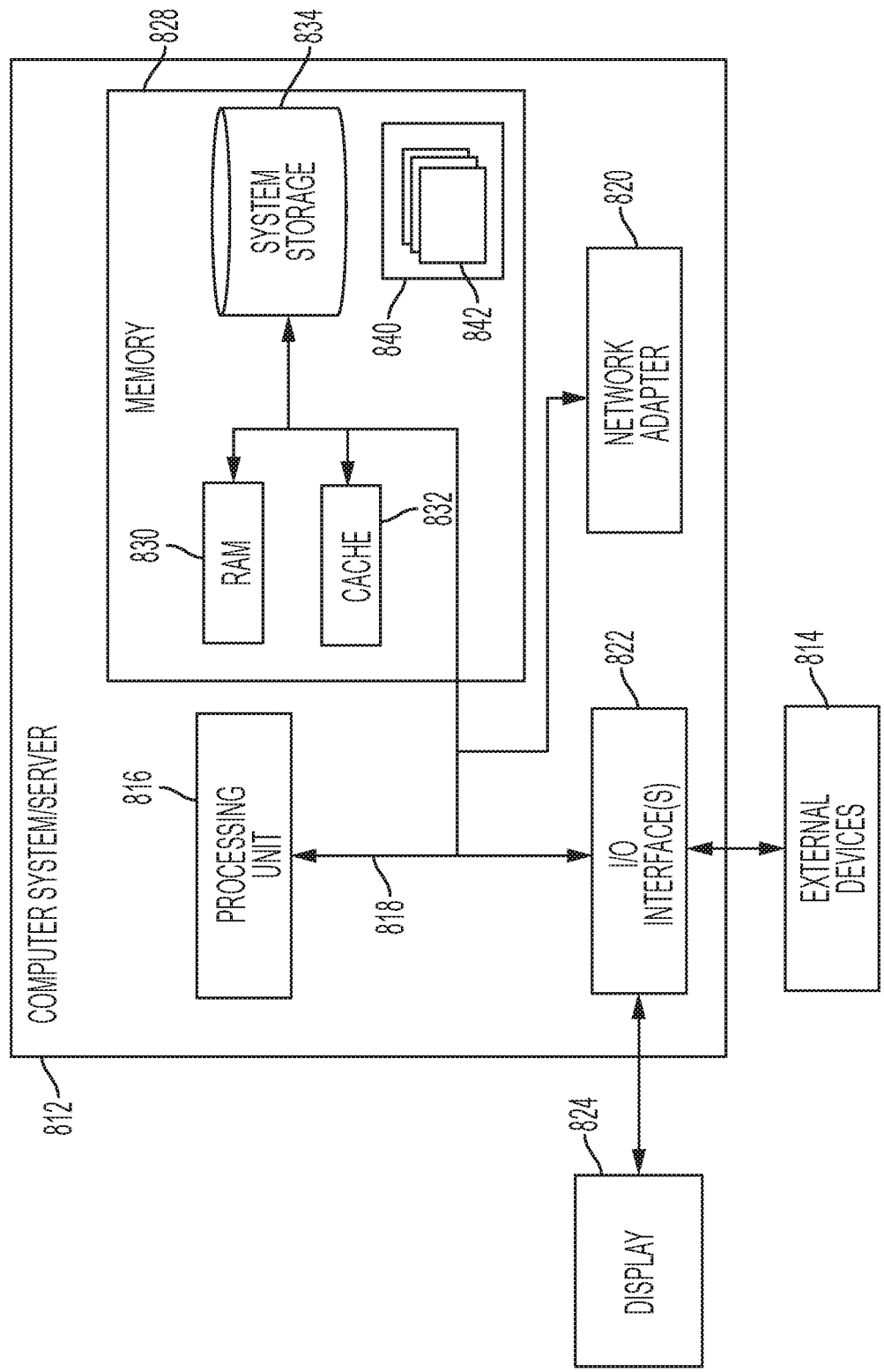
FIG. 8 depicts a schematic of an example computing system having elements and functions which operate as discussed herein according to embodiments of the invention.

FIG. 8 depicts a schematic of an example computing system 812 according to embodiments of the present invention. The computer system/server 812 can be operational with numerous other general purpose or special purpose computing system environments or configurations. The computer system/server 812 can be representative of various types of computer systems on which the optimization (and query) can run.

Examples of well-known computing systems, environments, and/or configurations that can be representative of and/or include elements of computer system/server 812 include, but are not limited to, personal computer systems, phones (e.g., cellphones, smart phones, etc.), server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 812 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 812 may be practiced in distributed cloud computing environments where tasks are performed by remote processing devices that are linked through a communications network. In a distributed cloud computing environment, program modules may be located in both local and remote computer system storage media including memory storage devices.

The components of computer system/server 812 may include, but are not limited to, one or more processors or processing units 816, a system memory 828, and a bus 818 that couples various system components including system memory 828 to processor 816. Bus 818 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 812 typically includes a variety of computer system readable media. Such media may be any available media that is accessible by computer system/server 812, and it includes both volatile and non-volatile media, removable and non-removable media. The system memory 828 can include computer system readable media in the form of volatile memory, such as random access memory (RAM) 380 and/or cache memory 832. Computer system/server 812 may further include other removable/non-removable, volatile/non-volatile computer system storage media. By way of example only, storage system 834 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 818 by one or more data media interfaces. Memory 828 may include at least one program product having a set (e.g., at least one) of program modules that are configured to carry out the functions of embodiments of the invention.

Program/utility 840, having a set (at least one) of program modules 842, may be stored in memory 828 by way of example, and not limitation, as well as an operating system, one or more application programs, other program modules, and program data. Each of the operating system, one or more application programs, other program modules, and program data or some combination thereof, may include an implementation of a networking environment. Program modules 842 generally carry out the functions and/or methodologies of embodiments of the invention as described herein.

Computer system/server 812 may also communicate with one or more external devices 814 such as a keyboard, a pointing device, a display 824, etc.; one or more devices that enable a user to interact with computer system/server 812; and/or any devices (e.g., network card, modem, etc.) that enable computer system/server 812 to communicate with one or more other computing devices. Such communication can occur via Input/Output (I/O) interfaces 822. Still yet, computer system/server 812 can communicate with one or more networks such as a local area network (LAN), a general wide area network (WAN), and/or a public network (e.g., the Internet) via network adapter 820. As depicted, network adapter 820 communicates with the other components of computer system/server 812 via bus 818. It should be understood that although not shown, other hardware and/or software components could be used in conjunction with computer system/server 812. Examples, include but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of forming an imaging apparatus, the method comprising:
   providing extensions coupled to a support structure, the extensions being spaced a predefined distance from one another, the extensions having a length that protrudes from the support structure;
   coupling light sources and therapeutic devices to the extensions such that the light sources are positioned to irradiate a scalp, the light sources and the therapeutic devices being coupled to the extensions such that one of the therapeutic devices and one of the light sources are on a same one of the extensions: and
   coupling sensors to the extensions, the sensors being configured downward facing to the scalp at an angle to capture images of the scalp having been irradiated by the light sources, the captured images of the scalp corresponding to locations of the extensions.
   wherein roller balls and pressure sensors are coupled to the distal ends of the extensions, ones of the roller balls being configured to individually engage ones of the pressure sensors.

2. The method of claim 1, wherein the extensions are spaced the predefined distance from one another so as to accommodate combing through hair on the scalp.

3. The method of claim 1, wherein the light sources are coupled to a distal end of the extensions.

4. The method of claim 1, wherein the light sources are positioned at a distance greater than half the length away from the support structure.

5. The method of claim 1, wherein the sensors are coupled to a distal end of the extensions.

6. The method of claim 1, wherein the sensors are positioned at a distance greater than half the length away from the support structure.

7. The method of claim 1, wherein the therapeutic devices are positioned at a distance greater than half the length away from the support structure.

8. The method of claim 1, wherein the therapeutic devices are positioned at an angle on the extensions to treat areas of the scalp.

9. An imaging apparatus, the apparatus comprising:
   extensions coupled to a support structure, the extensions being spaced a predefined distance from one another, the extensions having a length that protrudes from the support structure;
   light sources and therapeutic devices coupled to the extensions such that the light sources are positioned to irradiate a scalp, the light sources and the therapeutic devices being coupled to the extensions such that one of the therapeutic devices and one of the light sources are on a same one of the extensions: and
   sensors coupled to the extensions, the sensors being configured downward facing to the scalp at an angle to capture images of the scalp having been irradiated by the light sources, the captured images of the scalp corresponding to locations of the extensions.
   wherein roller balls and pressure sensors are coupled to the distal ends of the extensions, ones of the roller balls being configured to individually engage ones of the pressure sensors.

10. The apparatus of claim 9, wherein the extensions are spaced the predefined distance from one another so as to accommodate combing through hair on the scalp.

11. The apparatus of claim 9, wherein the light sources are coupled to a distal end of the extensions.

12. The apparatus of claim 9, wherein the light sources are positioned at a distance greater than half the length away from the support structure.

13. The apparatus of claim 9, wherein the sensors are coupled to a distal end of the extensions.

14. The apparatus of claim 9, wherein the sensors are positioned at a distance greater than half the length away from the support structure.

15. The apparatus of claim 9, wherein:
   the therapeutic devices are positioned at a distance greater than half the length away from the support structure;
   the therapeutic devices are positioned at angle on the extensions to treat areas of the scalp; and
   roller balls are coupled to ends of the extensions.

16. A method of operating an imaging apparatus, the method comprising:
   receiving, by the comb apparatus, location reference signals;
   capturing, by sensors positioned on extensions of the comb apparatus, images of a scalp at different locations on the scalp, the different locations of the images being determined based on the location reference signals, the images being captured under illumination from light sources of the comb apparatus, the sensors being configured downward facing to the scalp at angles on the extensions to capture the images of the scalp, wherein light sources and therapeutic devices are coupled to the extensions such that the light sources are positioned to irradiate a scalp, the light sources and the therapeutic devices being coupled to the extensions such that one of the therapeutic devices and one of the light sources are on a same one of the extensions; and
   wherein roller balls and pressure sensors are coupled to the distal ends of the extensions, ones of the roller balls being configured to individually engage ones of the pressure sensors.
   providing a model of the scalp according to the images captured at the different locations on the scalp.

17. The method of claim 16 further comprising:
   receiving a treatment plan for the scalp according the model; and
   causing the therapeutic devices of the comb apparatus to apply medical treatment to the scalp according to instructions of the treatment plan.

* * * * *